United States Patent [19]

Yasuhara et al.

[11] Patent Number: 4,646,070
[45] Date of Patent: Feb. 24, 1987

[54] OIL DETERIORATION DETECTOR METHOD AND APPARATUS

[75] Inventors: Seishi Yasuhara, Yokosuka; Hiroshi Kobayashi, Yokohama; Toru Kita, Yokosuka; Hideyuki Saito, Tokyo, all of Japan

[73] Assignee: Nissan Motor Company, Limited, Japan

[21] Appl. No.: 441,035

[22] Filed: Nov. 12, 1982

[30] Foreign Application Priority Data

Nov. 17, 1981 [JP] Japan ............................... 56-182996

[51] Int. Cl.$^4$ .............................................. G08B 21/00
[52] U.S. Cl. ........................................ 340/603; 73/64;
324/61 R; 331/65; 340/59; 340/631
[58] Field of Search ....................... 340/603, 604, 631;
324/61 R, 61 P, 61 QS, 61 QL; 73/61 R, 61.1 R, 64; 331/64, 65

[56] References Cited

U.S. PATENT DOCUMENTS

| | | | |
|---|---|---|---|
| 2,460,199 | 1/1949 | Taylor et al. | 331/64 X |
| 2,996,915 | 8/1961 | Greenwood et al. | 73/304 C |
| 3,067,385 | 12/1962 | Rykoskey | 324/61 R |
| 3,254,333 | 5/1966 | Baumoel | 331/64 |
| 3,631,436 | 12/1971 | Taguchi | 340/634 X |
| 3,675,121 | 7/1972 | Thompson | 324/61 R |
| 3,739,265 | 6/1973 | Skildum | 324/61 R |
| 3,746,974 | 7/1973 | Stoakes et al. | 324/61 R |
| 3,816,811 | 6/1974 | Cmelik | 324/61 R |
| 3,876,935 | 4/1975 | Guillermie et al. | 340/631 X |
| 3,882,478 | 5/1975 | Skarman | 340/634 X |
| 4,112,744 | 9/1978 | Tassano | 73/61.1 R |

FOREIGN PATENT DOCUMENTS

| | | |
|---|---|---|
| 0001919 | 5/1979 | European Pat. Off. . |
| 2120744 | 12/1971 | Fed. Rep. of Germany . |
| 7417295 | 3/1975 | France ............................ 324/61 R |

OTHER PUBLICATIONS

J. Blom, Journal of Physical Electronics; Scientific Instrumentation, vol. 12, No. 9, pp. 889–893 (Sep. 1979).

*Primary Examiner*—James L. Rowland
*Assistant Examiner*—Daniel Myer
*Attorney, Agent, or Firm*—Lowe, Price, LeBlanc, Becker & Shur

[57] ABSTRACT

The degree of deterioration of lubricating oil used in an internal combustion engine is detected by measuring the lubricating oil dielectric constant with a pair of spaced sensor capacitor electrodes in the lubricating oil. The sensor capacitor is connected to a fixed capacitor to form a voltage divider connected across a constant frequency AC voltage source so that a developed voltage across the sensor capacitor corresponds to the lubricating oil dielectric constant. The frequency of the AC voltage is set at a value ranging from 50 KHz to 500 KHz.

13 Claims, 15 Drawing Figures

OIL DETERIORATION DETECTOR METHOD AND APPARATUS

BACKGROUND OF THE INVENTION

This invention relates to an apparatus for and method of detecting the degree of deterioration of lubricating oil used in an internal combustion engine and, more particularly, to such an apparatus utilizing a pair of spaced apart electrodes dipped into the lubricating oil to form a sensor capacitor having a capacity that varies as a function of the lubricating oil dielectric constant.

When lubricating oil becomes deteriorated its lubricating ability is reduced due to contaminants, such as soot, which mix with the oil during use in an internal combustion engine. It is desirable to know the lubricating oil contamination state to signal when the oil should be changed.

In order to determine the degree of deterioration of lubricating oil, it has been the practice in the past to measure the conductivity of the lubricating oil by sensing current flow between a pair of electrodes dipped in the lubricating oil within an oil pan. However, the conductivity of lubricating oil varies to such an extent with oil temperature and brand as to completely invalidate the expected relationship between the lubricating oil conductivity measurement and the lubricating oil degree of deterioration. This is true particularly for diesel engines where a great amount of soot enters lubricating oil.

Therefore, the present invention provides an apparatus for and method of detecting the degree of deterioration of lubricating oil with greater accuracy independently of lubricating oil temperature and brand. Applicants have found that variations in the capacity or impedance of a sensor capacitor comprised of a pair of spaced apart electrodes dipped into lubricating oil corresponded relatively accurately with the extent to which the lubricating oil is deteriorated. The present invention utilizes the variations of the sensor capacitor as an indicator of oil deterioration.

SUMMARY OF THE INVENTION

There is provided, in accordance with the present invention, an apparatus for detecting the degree of deterioration of lubricating oil used in an internal combustion engine. The apparatus comprises a sensor including a pair of spaced apart electrodes dipped into the lubricating oil to form a sensor capacitor having a capacity that varies as a function of the dielectric constant of the lubricating oil. A constant frequency AC voltage is applied to the sensor capacitor so that the sensor generates an output corresponding to the dielectric constant of the lubricating oil. The output of the sensor is applied to an oil deterioration indicator which thereby indicates the degree of deterioration of the lubricating oil corresponding to the sensed lubricating oil dielectric constant. The frequency of the AC voltage is set within a range of 50 KHz to 500 KHz. This is effective to avoid adverse influences of oil temperature changes on the measurement of the dielectric constant of the lubricating oil.

BRIEF DESCRIPTION OF THE DRAWINGS

The details as well as other features and advantages of this invention are set forth below and are shown in the accompanying drawings, in which.

DETAILED DESCRIPTION OF THE INVENTION

Figure 1:
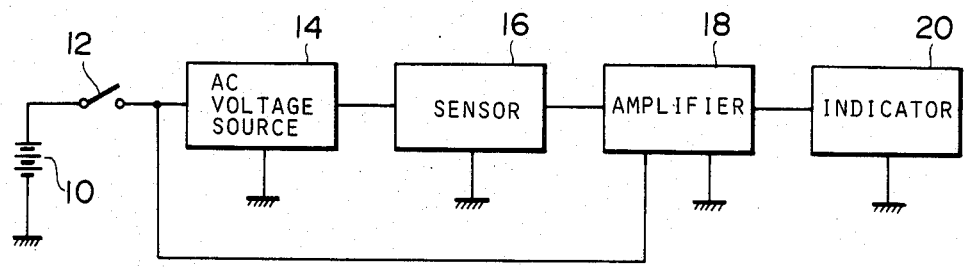
FIG. 1 is a block diagram of one emodiment of an oil deterioration detector in accordance with the present invention.

Referring now to FIG. 1 of the drawings, one embodiment of an oil deterioration detecting apparatus in accordance with the present invention is illustrated as including a DC power source 10 connected through a main switch 12 to an AC voltage generator 14. The AC voltage generator 14 comprises an RC oscillator or a crystal oscillator for generating a constant frequency AC voltage when the main switch 12 is closed. The frequency of the AC voltage is within a range of 50 KHz to 500 KHz for reasons described in detail infra. The AC voltage is applied to a sensor 16 which generates an AC voltage corresponding to the degree of deterioration of an engine oil used in an internal combustion engine. The output of the sensor 16 is coupled through an amplifier 18 to an oil deterioration indicator 20 for providing an indication of the sensed degree of oil deterioration.

Figure 2:
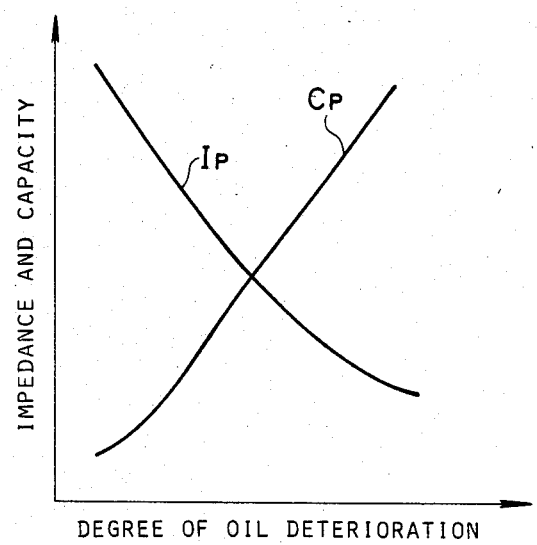
FIG. 2 is a graph of variations in the impedance and capacity of the sensor capacitor as a function of lubricating oil deterioration.

The sensor 16 includes a sensor capacitor having a pair of spaced apart electrodes dipped into the lubricating oil so that the sensor capacitor has a capacity of more than 400 PF to avoid any adverse influence of floating capacity. For example, the electrodes may be formed of plates having an area of about 200 cm$^2$ spaced apart from each other by a distance of about 1 mm. The impedance and capacity of the sensor capacitor vary as a function of the dielectric constant or permittivity of the lubricating oil, as shown in FIG. 2. As the lubricating oil deterioration increases its dielectric constant increases, causing (1) the sensor capacitor impedance to decrease, as illustrated by the impedance versus oil deterioration curve IP, and (2) the sensor capacitor capacity to increase, as illustrated by capacity versus oil deterioration curve CP. The device also includes a circuit which connects the sensor capacitor to the AC voltage source 14 for generating a sensor output corresponding to the dielectric constant of the lubricating oil.

The circuit is preferably in the form of a capacitor having a fixed capacity, in which case the capacitor is connected in series with the sensor capacitor to form a voltage divider which divides the output voltage of the AC voltage generator 14 by a factor determined by the dielectric constant of the lubricating oil so that the AC voltage across the sensor capacitor is substantially proportional to the engine oil dielectric constant.

Figure 3A:
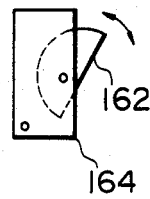
FIGS. 3A, 3B and 3C are diagrams of two different forms of the sensor capacitor.
Figure 3B:
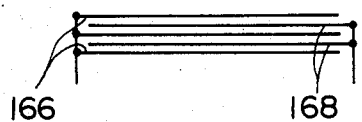
Figure 3C:
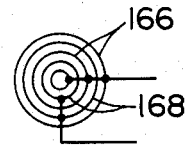

The sensor capacitor in the embodiment of FIG. 3A is a variable capacitor comprising one set of parallel plates 162 moving in relation to another set of parallel plates 164 to have every possible capacity value within its range. Alternatively, the sensor capacitor has one set of concentrically arranged cylindrical plates 166 placed in relation to another set of concentrically arranged cylindrical plates 168 as shown in FIGS. 3B and 3C. Such capacitor arrangements are effective to reduce the sensor size and facilitate movement of the lubricating oil through the sensor capacitor. The sensor capacitor may also be a printed electrode plate having a desired electrode pattern printed on a tip plate.

Figure 4A:
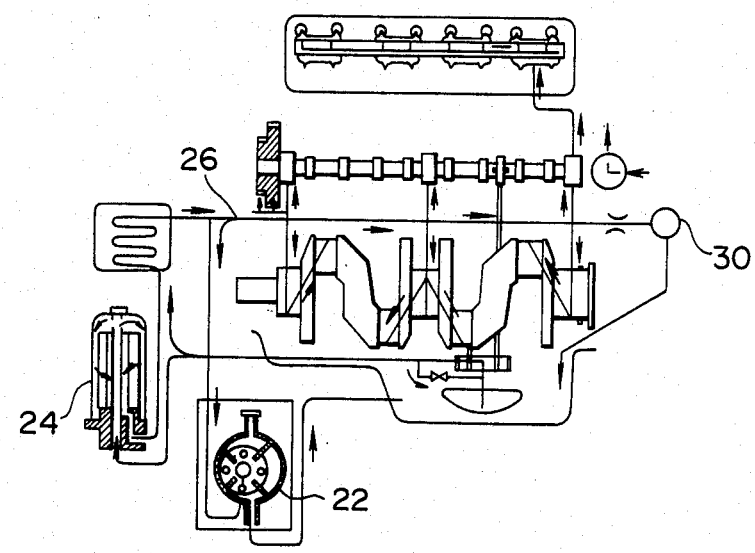
FIGS. 4A and 4B are schematic views of a lubrication system in which the sensor capacitor is placed.
Figure 4B:
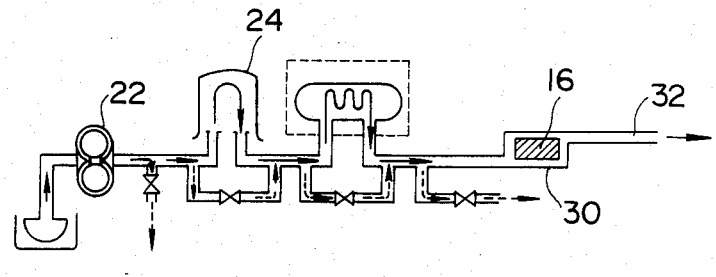
Figure 5:
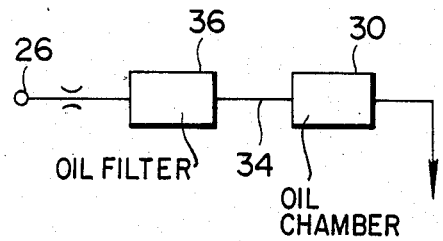
FIG. 5 is a schematic view of a lubrication system oil passage in which the sensor capacitor is placed.

Referring to FIGS. 4A and 4B, there is illustrated a lubrication system which includes a pump 22 for supplying engine oil under pressure through an oil filter 24 to a crank case 26. The sensor capacitor 16 is located in an oil chamber 30 formed in an oil passage 28 downstream of the crank case 26 or in an oil passage 32 downstream of the oil filter 24. The oil chamber 30 may be located in another suitable position as long as there is a minimum amount of contaminants and the engine oil flows at a relatively high rate in order to keep the sensor capacitor free from deposits on its electrode surfaces. This is effective to minimize changes in the sensor capacitor characteristics with time. Alternatively, as illustrated in FIG. 5 the oil chamber 30 may be formed in a return passage 34 leading to an oil pan with another oil filter 36 being positioned in the return passage 34 upstream of the oil chamber 30.

Figure 6:
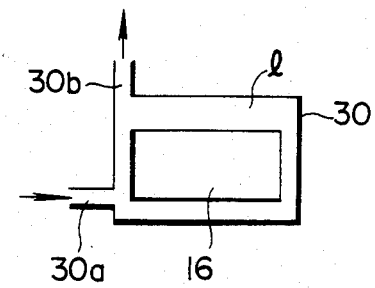
FIG. 6 is a diagram of an oil chamber formed in the lubrication system containing the sensor capacitor.

Referring to FIG. 6, the oil chamber 30, which contains the sensor capacitor 16, has an inlet 30a formed near the chamber bottom, and an outlet 30b, formed in the chamber upper wall so that an air pocket does not form in the oil chamber 30. Preferably, the sensor capacitor 16 is placed in the oil chamber 30 to provide a space of 1 between the capacitor electrodes and the oil chamber upper wall. The sensor electrodes extend vertically toward the oil chamber upper wall to prevent formation of air bubbles between the sensor capacitor electrodes; the air bubbles change the capacity of the sensor capacitor. The surfaces of the sensor capacitor electrodes are coated with a corrosion protective material, such as fluorocarbon polymers, to protect the surfaces against acids and bases in the lubricating oil. This also prevents DC conduction due to entrance of contaminants between the sensor capacitor electrodes.

The output of the sensor 16 is applied to an amplifier 18 which amplifies the AC voltage across the sensor capacitor and applies the amplified AC voltage to the oil deterioration indicator 20. The amplifier 18 may have an additional function of converting the amplified AC voltage value into a corresponding DC voltage value.

Figure 7:
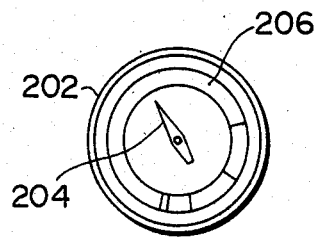
FIG. 7 is an elevation view of a gauge included in the oil deterioration indicator of FIG. 1.
Figure 8:
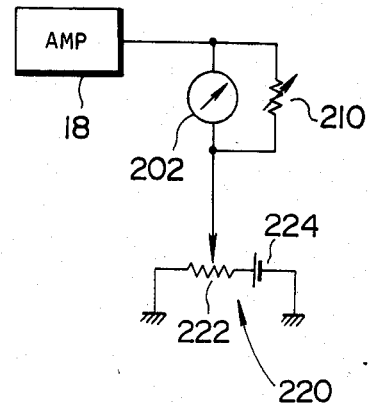
FIG. 8 is a circuit diagram of a circuit for calibrating the gauge of FIG. 3.

Referring to FIGS. 7 and 8, the oil deterioration indicator 20 includes a meter 202 having a pointer 204 and an indicator scale 206 with ranges classified by color. The meter 202 is associated with a sensitivity adjusting circuit 210 and a zero setting circuit 220. The sensitivity adjusting circuit 210 includes a variable resistor for adjusting the sensitivity of the gauge meter by varying the meter resistance within its range. The zero setting circuit 220 comprises a potentiometer 222 connected between a DC power source 224 and electrical ground. The wiper arm of the potentiometer 222, connected to one end of the meter 202, is moved to set the gauge pointer 204 to correspond with the scale zero. The other end of the meter 202 is connected to the output of the amplifier 18 so that the pointer 204 turns through an angle corresponding to the output of the amplifier 18 to point to a colored scale range which indicates the degree of engine oil deterioration.

Figure 9:
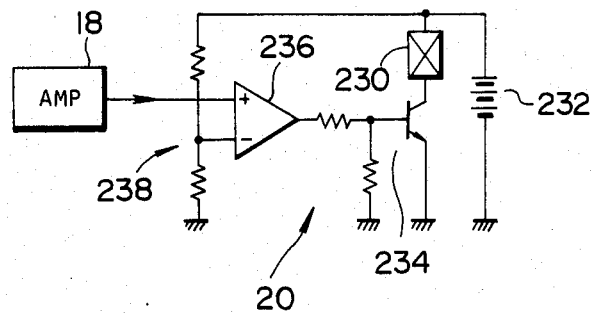
FIG. 9 is a circuit diagram of a modified form of the oil deterioration indicator.

Referring to FIG. 9, there is illustrated a modification of the oil deterioration indicator 20 that comprises a buzzer 230, having opposite terminals connected to a DC power source 232 and the collector of a transistor 234, having a grounded emitter. The base of the transistor 234 is connected through a resistor to the output of a comparator 236 which has a positive input terminal connected to the output of the amplifier 18 (FIG. 1). The negative input terminal of the comparator 236 is connected to a reference voltage source 238, formed of a voltage divider connected across the DC voltage source 232; the input of amplifier 236 from divider 238 is a reference voltage which represents a reference oil deterioration degree at which the engine oil is required to be changed. When the output of the amplifier 18 reaches the reference voltage, the comparator 236 generates a high output which forward biases the transistor 234 to sound the buzzer 230. The indicator 20 may include a conventional oil-pressure light which is illuminated whenever the oil pressure is below a predetermined level. In this case, the oil-pressure light may come on at predetermined intervals when the oil deterioration degree reaches the reference value to distinguish the oil deterioration degree indication from the insufficient oil pressure indication.

Figure 10:
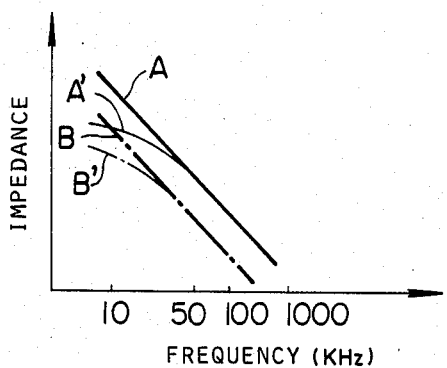
FIG. 10 is a comparative graph of impedance versus AC voltage frequency curves obtained on new and used lubricating oil at low and high temperatures.
Figure 11:
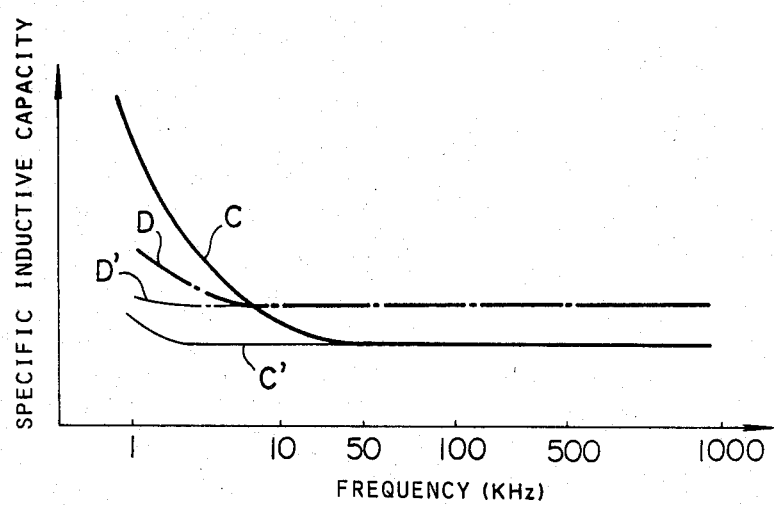
FIG. 11 is a comparative graph of specified inductive capacity versus AC voltage frequency curves obtained for new and used lubricating oil at low and high temperatures.

FIG. 10 includes comparative curves of impedance versus frequency. Curve A is for new engine oil at high temperature, while curve A' is for new engine oil at low temperature. Curve B is for used engine oil at high temperature, while curve B' is for used engine oil at low temperature. From FIG. 10 it is seen that there is a greater change in the impedance of the sensor capacitor as the engine temperature changes than there is due to oil deterioration when the frequency of the AC voltage applied to the sensor capacitor is below about 50 KHz. Comparative specific inductive capacity curves are included in FIG. 11. Curve C is for new engine oil at high temperature while curve C' is for new engine oil at low temperature. Curve D is for used engine oil at high temperature while curve D' is for used engine oil at low temperature. From FIG. 11, a greater change is caused in the specific inductive capacity of the engine oil by engine temperature changes than is caused by oil deterioration when the frequency of the AC voltage applied to the sensor capacitor is below about 50 KHz.

The frequency of the AC voltage applied by the AC voltage generator 14 to the sensor 16 is set at a value in the range of 50 KHz to 500 KHz. If the frequency is lower than this range, the oil deterioration sensed by sensor 16 is influenced by engine temperature changes, causing an improper indication of oil deterioration degree. If AC frequency is higher than 500 KHz, radio interference from the AM radio band occurs. Preferably, the frequency is set at 100 KHz. Experiments show that any deviation which appears in the output of the sensor 18 due to use of lubrication oil of different brands can be ignored in practice.

Figure 12:
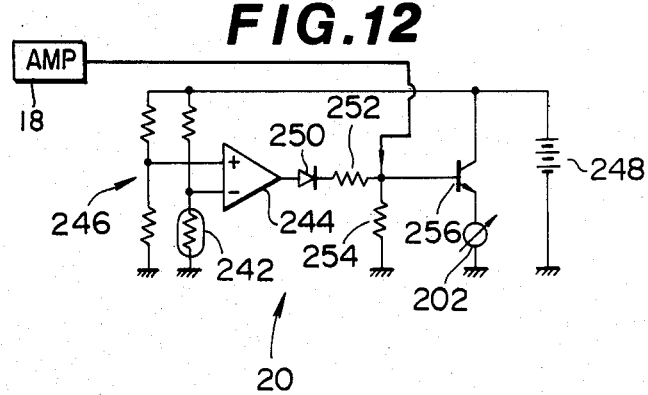
FIG. 12 is a circuit diagram of a modified form of the oil deterioration indicator.

Referring to FIG. 12, there is illustrated an alternative form of the oil deterioration indicator 20 wherein a circuit associated with the meter 202 is operative only when the engine temperature is above a predetermined value, for example, 80° C. This avoids adverse influences of engine temperature changes on the indication of oil deterioration degree. The circuit comprises a thermistor 242 connected in an electrical circuit capable of producing a DC voltage having a variable level corresponding to the engine temperature represented by the engine coolant temperature. The output of the thermistor 242 is connected to the negative input terminal of a comparator 244 having a positive input terminal connected to a reference voltage source 246, formed as a voltage divider connected across a DC voltage source 248; the reference voltage represents a predetermined temperature value. The output of the comparator 244 is connected by the series combination of diode 250 and resistor 253 to the base of a transistor 256 having an emitter grounded through meter 202. The collector of the transistor 256 is connected to the positive terminal of the DC power source 248. The base of the transistor 256 is connected by resistor 254 to ground and to the output of the amplifier 18. When the engine coolant temperature reaches the predetermined value, the comparator 244 generates a high output which forward biases transistor 254 to place the meter 202 in operation.

While the present invention has been described in conjunction with specific embodiments thereof, it is evident that many alternatives, modifications and variations will be apparent to those skilled in the art. Accordingly, it is intended to embrace all alternatives, modifications and variations that fall within the spirit and broad scope of the appended claims.

What is claimed is:

1. An apparatus for detecting the degree of deterioration of lubricating oil used in an internal combustion engine, comprising:
    (a) an AC voltage source for generating an AC voltage of a predetermined frequency ranging from about 50 KHz to about 500 KHz;
    (b) a sensor including a pair of spaced apart electrodes dipped into the lubricating oil while the oil is in the internal combustion engine, the electrodes and the oil between them forming a sensor capacitor having a capacity that varies as a function of the lubricating oil dielectric constant, circuit means for connecting said sensor capacitor to said AC voltage source and for generating an output having a value corresponding to the lubricating oil dielectric constant; and
    (c) an indicator connected to be responsive to said output for indicating oil deterioration degree corresponding to the output of said sensor, said indicator being arranged to indicate that the oil deterioration degree is relatively low and high in response to the impedance between the electrodes being respectively relatively high and low, whereby the indicator response is independent of temperature of the oil for oil temperatures above a predetermined level corresponding with operation of the internal combustion engine.

2. The apparatus of claim 1, wherein said AC voltage source generates a constant frequency of 100 KHz.

3. The apparatus of claim 1, wherein said indicator includes meter means for providing an oil deterioration degree indication corresponding to the output of said sensor, and means for deactivating said meter means while the engine oil temperature is less than the predetermined level.

4. The apparatus of claim 1, wherein said indicator includes a buzzer and means for activating said buzzer in response to the output of said sensor reaching a predetermined value.

5. The apparatus of claim 1, wherein said sensor capacitor comprises a variable capacitor including one set of parallel metal plates movable in relation to another set of parallel metal plates to have every possible value of capacity within its range.

6. The apparatus of claim 1, wherein said sensor capacitor includes a first set of concentrically arranged cylindrical metal plates and a second set of concentrically arranged cylindrical metal plates, said first and second sets of plates being positioned adjacent each other so they are coupled to each other and the oil being measured.

7. The apparatus of claim 1, wherein said circuit includes a capacitor of a fixed capacity, said fixed capacity capacitor being connected in series with said sensor capacitor to form a voltage divider connected across said AC voltage source so that an AC voltage corresponding to the lubricating oil dielectric constant is developed across said sensor capacitor.

8. A method of determining the degree of deterioration of lubricating oil in an operating internal combustion engine comprising the steps of measuring the capacitance of the oil by applying AC electric energy having a frequency of at least 50 KHz across a pair of electrodes in the oil while the engine is operating, and indicating that the measured oil has relatively low and high deterioration degrees in response to the measured capacitance being respectively relatively low and high, whereby the indication of the deterioration degree of the oil is independent of the oil temperature for oil temperatures above a predetermined level corresponding with operation of the internal combustion engine.

9. The method of claim 8, further including the step of inhibiting the maximum frequency of the AC waves to 500 KHz, whereby RF interference with the indication of the deterioration degree of the oil is minimized.

10. The method of claim 9, further including the step of inhibiting the indicating step for oil temperatures less than 80° C.

11. The method of claim 8, further including the step of inhibiting the indicating step for oil temperatures less than 80° C.

12. A method of determining the degree of deterioration of lubricating oil in an operating internal combustion engine comprising the steps of measuring the impedance between a pair of capacitor electrodes in the oil while the engine is operating, indicating that the measured oil has relatively low and high deterioration degrees in response to the measured impedance being respectively relatively high and low, and inhibiting the indicating step while the oil temperature is less than 80° C. whereby the indication of the deterioration degree of the oil is independent of the oil temperature.

13. The method of claim 12, further including the step of inhibiting the maximum frequency of the AC waves to 500 KHz, whereby RF interference with the indication of the deterioration degree of the oil is minimized.

* * * * *